April 23, 1968 M. A. LOGAN Plant Pat. 2,807
PEACH TREE
Filed Dec. 16, 1966
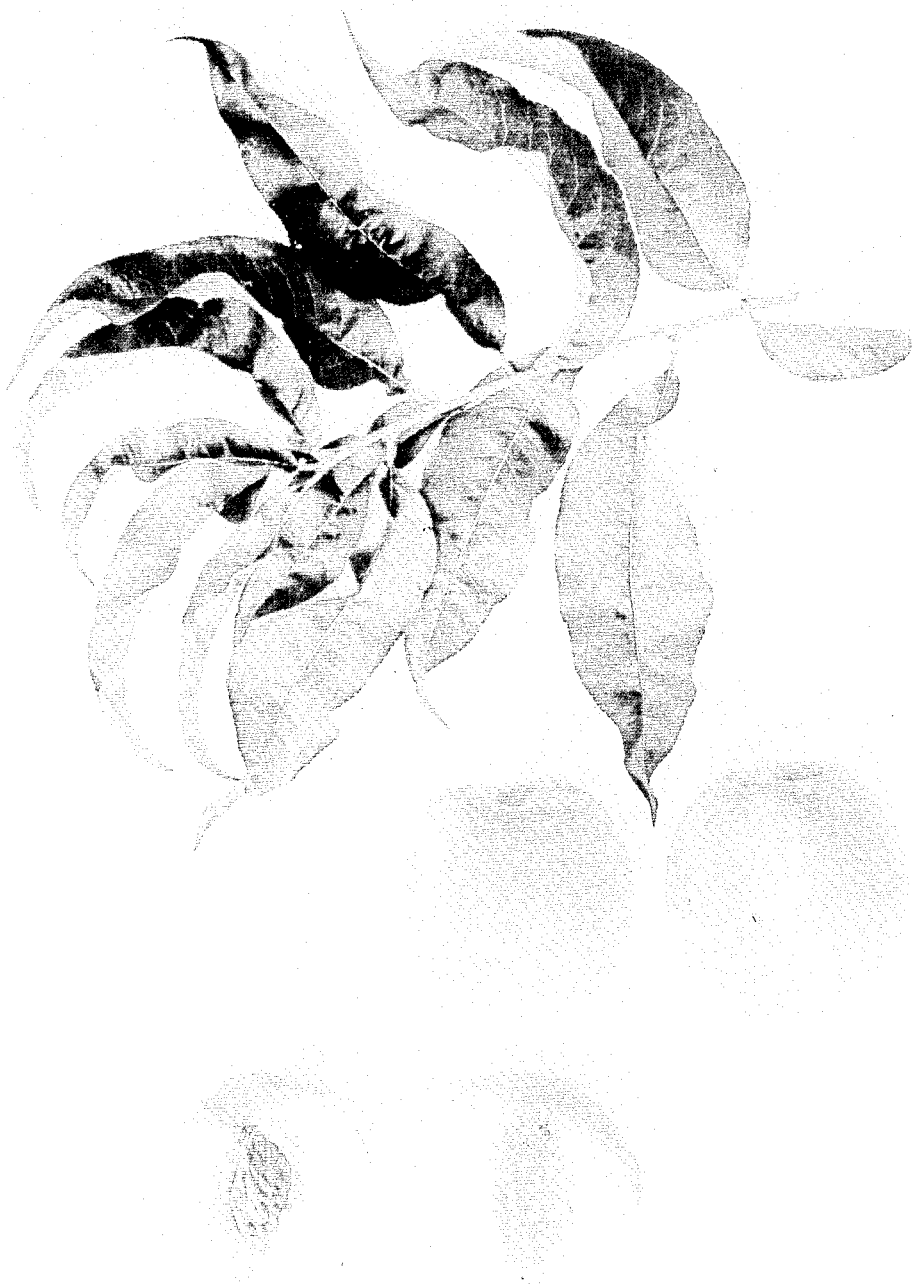
INVENTOR
Mabel A. Logan
BY
Webster & Webster
ATTORNEYS United States Patent Office Plant Pat. 2,807
Patented Apr. 23, 1968

2,807
PEACH TREE

Mabel A. Logan, Rte. 2, Box 1269,
Grass Valley, Calif. 95945

Filed Dec. 16, 1966, Ser. No. 602,430
1 Claim. (Cl. Plt.—43)

This discovery relates to a new and distinct variety of peach tree which is a regular and very productive bearer of large, globose, freestone fruit having golden yellow flesh streaked with red adjacent the pit cavity, and yellow skin partially overspread and mottled with red.

The present variety of peach tree is particularly characterized, as to novelty, by a late season ripening period of excellent fruit and which is of good eating quality and delicious flavor; such fruit being in harvest about three weeks after the Rio Oso Gem (United States Plant Patent No. 84).

The herein claimed variety of peach tree was discovered by me growing as a chance seedling in the yard of my residence located in the Cedar Ridge area near Grass Valley, Nevada County, Calif. When such chance seedling, which was maintained under care, began to bear fruit I recognized—upon close and continuing observation—that such seedling was quite different in comparison to other peach varieties, both in the character and quality of the fruit and the ripening period.

Subsequent to recognition by me that the variety was novel and distinct, such variety was asexually reproduced—upon my order and on my behalf—by a commercial nursery at its Mt. Pleasant growing grounds located near Lincoln, Placer County, Calif.; such asexual reproduction having been accomplished by budding onto Lovell (unpatented) rootstock. All of such asexual reproductions were found to run true to the original tree in all respects.

The drawing is an illustration, by photographic reproduction in color, of a twig with leaves, two whole fruit, and another fruit cut in half to expose the flesh and with the stone remaining in one half.

Referring now more specifically to the pomological details of this new and distinct variety of peach tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Medium.
- *Growth.*—Upright.
- *Density.*—Open.
- *Form.*—Vase-formed.
- *Hardiness.*—Half hardy.
- *Production.*—Very productive.
- *Bearing.*—Regular bearer.

Trunk:
- *Size.*—Medium—slender.
- *Texture.*—Medium.

Branches:
- *Size.*—Medium.
- *Texture.*—Medium.
- *Color.*—Dull reddish-brown.
- *Lenticels.*—Number—few. Size—small.

Leaves:
- *Size.*—Medium. Average length—5". Average width—1⅝".
- *Form.*—Lanceolate; acutely pointed.
- *Thickness.*—Medium.
- *Texture.*—Smooth.
- *Margin.*—Glandular; finely serrate.

- *Petiole.*—Medium length; medium thickness.
- *Glands.*—Average number—2. Opposite; small; globose; green; positioned on petiole adjacent base of blade.
- *Stipules.*—Present.
- *Color.*—Top side—glossy medium green (23–L–8). Under side—lighter green (22–J–5).

Flower buds:
- *Hardiness.*—Half hardy.
- *Size.*—Medium.
- *Length.*—Short.
- *Form.*—Pointed; plump; free.

Flowers:
- *Blooming period.*—Date of first bloom—Mar. 7, 1966. Date of full bloom—Mar. 17, 1966. Medium, as compared with other varieties.
- *Size.*—Large.
- *Color.*—Pink.

Fruit:
- *Maturity when described.*—Eating ripe—first week in September.
- *Date of first picking.*—Sept. 1, 1966.
- *Date of last picking.*—Sept. 7, 1966.
- *Size.*—Uniform; large. Average diameter axially—3". Average transversely in suture plane—2¾".
- *Form.*—Uniform; symmetrical; globose.
- *Suture.*—Shallow, with slight depression beyond pistil point.
- *Ventral surface.*—Rounded slightly; lipped toward both sides.
- *Lips.*—Equal.
- *Cavity.*—Circular; elongated in suture plane with suture showing on one side. Average depth—⅜". Average breadth—⅜".
- *Base.*—Rounded.
- *Apex.*—Rounded.
- *Pistil point.*—Oblique.

Skin:
- *Thickness.*—Medium.
- *Texture.*—Medium.
- *Tenacity.*—Free.
- *Tendency to crack.*—None.
- *Down.*—Moderate.
- *Color.*—Yellow (11–L–5) partially overspread and mottled with red (5–L–8).

Flesh:
- *Amygdalin.*—Scant.
- *Juice.*—Abundant; rich.
- *Texture.*—Firm.
- *Fibers.*—Few; fine.
- *Ripens.*—Evenly.
- *Flavor.*—Subacid; mild.
- *Aroma.*—Distinct.
- *Eating quality.*—Best.
- *Color.*—Golden yellow (10–L–7), streaked with red (5–L–4) adjacent the pit cavity. Surface of pit cavity—red (5–L–4).

Stone:
- *Type.*—Free; parts from flesh smoothly.
- *Size.*—Medium. Average length—1". Average breadth—⅝". Average thickness—½".
- *Fibers.*—Short.
- *Form.*—Elliptical.
- *Base.*—Oblique.
- *Hilum.*—Narrow.
- *Apex.*—Acute.
- *Sides.*—Equal.
- *Surface.*—Regularly furrowed toward apex; ridged throughout.
- *Ridges.*—Jagged; continuous.
- *Pits.*—Elongated.

*Ventral edge.*—Thin, with wing throughout.
*Dorsal edge.*—Full, with broad groove throughout.
*Tendency to split.*—Slight.
*Color.*—Medium brown (8–H–6), with reddish tinge.
Use: Market—local. Dessert.
Keeping quality: Good.
Shipping quality: Good.

The tree and its fruit herein described may vary in slight detail due to climatic and soil conditions under which the variety may be grown; the present description being of the variety as grown in the foothill region of northern California.

The following is claimed:

A new and distinct variety of peach tree, substantially as illustrated and described, characterized by the regular and very productive bearing of large, freestone, globose fruit having golden yellow flesh streaked with red adjacent the pit cavity, and yellow skin partially overspread and mottled with red; and further characterized by a ripening period of the fruit about three weeks after the Rio Oso Gem.

No references cited.

ROBERT E. BAGWILL, *Primary Examiner.*